US00RE37355B1

(19) United States
(12) Reissued Patent
Buschmann et al.

(10) Patent Number: US RE37,355 E
(45) Date of Reissued Patent: Sep. 4, 2001

(54) 6-DIMETHYLAMINOMETHYL-1-PHENYL-CYCLOHEXANE COMPOUNDS AS PHARMACEUTICAL ACTIVE INGREDIENTS

(75) Inventors: Helmut Heinrich Buschmann, Aachen; Wolfgang Werner Alfred Strassburger, Wuerselen; Norma Selve, Berlin; Elmar Josef Friderichs, Stolberg, all of (DE)

(73) Assignee: Gruenenthal GmbH, Aachen (DE)

(21) Appl. No.: 09/539,528

(22) Filed: Mar. 30, 2000

Related U.S. Patent Documents

Reissue of:
(64) Patent No.: 5,733,936
Issued: Mar. 31, 1998
Appl. No.: 08/679,756
Filed: Jul. 10, 1996

(30) Foreign Application Priority Data

Jul. 11, 1995 (DE) ..... 195 25 137

(51) Int. Cl.[7] ..... A61K 31/135; A61K 31/21; A61K 31/16; A61K 31/44; A61K 31/425; A61K 31/38; C07C 211/35; C07D 211/72

(52) U.S. Cl. ..... 514/646; 514/506; 514/620; 514/349; 514/369; 514/445; 564/305; 560/39; 558/70; 546/300; 548/189; 549/65

(58) Field of Search ..... 514/646, 506, 514/620, 349, 369, 445; 564/305; 560/39; 558/70; 546/300; 548/189; 5499/65

(56) References Cited

U.S. PATENT DOCUMENTS 3,652,589 * 3/1972 Flick et al. ..... 564/305

OTHER PUBLICATIONS

Sauda et al. (I) "Aralkylcyclohexanemethylamines", CA 88: 22336, 1988.*
Sawa et al (II), "Phenylcyclohexane and Benzylcyclohexane derivatives", CA 87: 52931, 1987.*
Bundgaard, *Drugs of the Future* 16 443 (1991).
Bundgaard et al., *J. Med. Chem.,* 32, 2503 (1989).
Craig et al., *J. Am. Chem. Soc.* 74, 1316 (1952).
D'Amour et al., *J. Pharm. Exp. Ther.* 72, 74–79 (1941).
Dittert et al., *J. Pharm. Sci.,* 57, 774 (1968).
Flick et al., *Arzneim.–Forsch./Drug Res.,* 28 (IA) 107 (1978).
Hudlicky, *Org. Reac.,* 35, 513 (1988).
Jaffe et al., Goodman, Gilman "The Pharmaceutical Basis of Therapeutics" Pergamon Press, New York, 1990, pp. 485–521.
Kato et al., *Chem. Pharm. Bull.* 32 2279 (1984).
Kim et al., *Angew. Chem.,* 95 568 (1983).
Litchfield et al., *J. Pharm. Exp. Ther.* 96, 99–113, (1949).
Olofson et al., *Tetrahedron Lett.,* 1977, 1571.
Raffa et al., *J. Pharmacol. Exp. Ther.,* 260, 275 (1992).
Raffa et al., *J. Pharmacol. Exp. Ther.,* 267, 331 (1993).
Smith et al., *J. Org. Chem.,* 17, 1116 (1952).
Thornberg et al., *J. Med. Chem.,* 30, 2008 (1989).
Tietze et al., "Reaktionen und Synthesen im Organisch–Chemischen Praktikum", ["Reactions and Synthesis in the Practice of Organic Chemistry"], Thieme–Verlag, Stuttgart 1991, p. 189.
Tramontini, *Synthesis,* 1973, 703.
Vogel, *J. Chem. Soc.,* 1943, 636.
Wang et al., *J. Org. Chem.,* 59, 6895 (1994).
Welch et al., *J. Org. Chem.,* 43, 4797 (1978).
Winterfeldt, *Synthesis,* 1975, 617.

* cited by examiner

*Primary Examiner*—Deborah C. Lambkin
(74) *Attorney, Agent, or Firm*—Evenson, McKeown, Edwards & Lenahan, P.L.L.C.

(57) ABSTRACT

6-dimethylaminomethyl-1-phenyl-cyclohexane compounds, methods of preparing them and the use of these compounds in drugs are described.

7 Claims, No Drawings

6-DIMETHYLAMINOMETHYL-1-PHENYL-CYCLOHEXANE COMPOUNDS AS PHARMACEUTICAL ACTIVE INGREDIENTS

Matter enclosed in heavy brackets [ ] appears in the original patent but forms no part of this reissue specification; matter printed in italics indicates the additions made by reissue.

BACKGROUND OF THE INVENTION

6dimethylaminomethyl-1-phenyl-cyclohexane compounds as pharmaceutical active ingredients This invention relates to 6-dimethylaminomethyl-1-phenyl-cyclohexane compounds, to methods of preparing them and to the use of these compounds in drugs.

The treatment of chronic and non-chronic pain conditions is of great importance in medicine. There is currently a world-wide need for additional pain therapy which is not exclusively opioid but which exhibits good efficacy. The pressing requirement for a target-oriented treatment of chronic and non-chronic pain conditions which is right for the patient, which is to be understood as the successful and satisfactory treatment of pain for the patients, is documented in the large number of scientific works which have recently appeared in the field of applied analgesics or on basic research on nociception.

Opioids have been used for many years for the treatment of pain, even though they give rise to a series of side effects, for example dependency, respiratory depression, gastrointestinal inhibition effects and obstipation. They can therefore only be given over an extended period of time or in high dosages subject to special precautions, for example special prescription regulations (Goodman, Gilman "The Pharmaceutical Basis of Therapeutics" Pergamon Press, New York, 1990).

Tramadol hydrochloride—(1RS,2RS)-2[(dimethylamino)methyl]-1-(3 -methoxyphenyl)cyclohexanol hydrochloride—assumes a special position amongst centrally acting analgesics, since this active ingredient acts as a strong inhibitor of pain without the side effects which are known for opioids (J. Pharmacol. Exp. Ther. 267, 331 (1993)). Tramadol is a racemate and consists of equal amounts of (+) and (−) enantiomers. In vivo, this active ingredient forms the metabolite O-desmethyl-tramadol, which likewise exists as a mixture of enantiomers. Investigations have shown that both the enantiomers of tramadol and the enantiomers of the tramadol metabolite have a part in the analgesic effect (J. Pharmacol. Exp. Ther. 260, 275 (1992)).

Compounds of formula

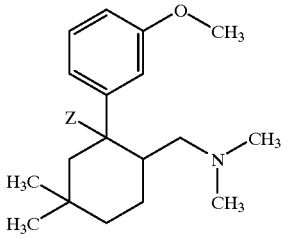

are known from Chem. Pharm. Bull. 32, 2279 (1984) in which Z represents H or OH These substances have an analgesic effect which is considerably weaker than that of tramadol.

SUMMARY OF THE INVENTION

The underlying object of the present invention was to develop substances with an analgesic effect which are suitable for the treatment of severe pain without giving rise to the side effects which are known for opioids. The object was also that the substances to be developed should not exhibit the side effects which occur in some cases of treatment with tramadol for example nausea and vomiting.

It has now been found that the requirements imposed on the substances to be developed are fulfilled by certain 6-dimethylaminomethyl-1-phenyl-cyclohexane compounds. These compounds are distinguished by a pronounced analgesic effect, which is significantly more intense compared with tramadol and with the compounds of formula

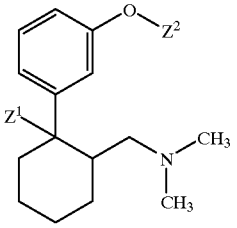

which are known from Arzneim.-Forsch./Drug Res. 28 (IA) 107 (1978), where $Z^1$ is H, OH or Cl and $Z^2$ is $CH_3$, or $Z^1$ is OH and $Z^2$ is H.

DETAILED DESCRIPTION OF PREFERRED EMBODIMENTS

Accordingly, the present invention relates to 6-dimethylaminomethyl-1-phenylcyclohexane compounds of formula I

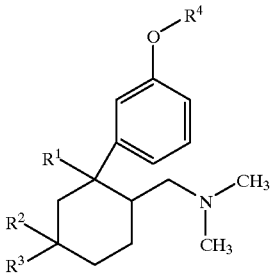

in which $R^1$ is H, OH, Cl or F, $R^2$ and $R^3$ are the same or different, and represent H, $C_{1-4}$ alkyl benzyl, $CF_3$, OH, $OCH_2$-$C_6H_5$, O—$C_{1-4}$-alkyl, Cl or F, with the proviso that at least one of the radicals $R^2$ or $R^3$ represents H, $R^4$ represents H, $CH_3$, $PO(OC_{1-4}\text{-alkyl})_2$, $CO(OC_{1-5}\text{-alkyl})$, CO—NH—$C_6H_4$-$C_{1-3}$-alkyl, CO—$C_6H_4$-$R^5$, CO—$C_{1-5}$-alkyl, CO—$CHR^6$-NHR or an unsubstituted or substituted pyridyl, thienyl, thiazoyl or phenyl group, $R^5$ represents $OC(O)C_{1-3}$-alkyl in the ortho position or $CH_2$-$N(R^8)_2$ in the meta or para position, wherein $R^8$ represents $C_{1-4}$ alkyl or both radicals $R^8$ together with N constitute the 4-morpholino radical, and $R^6$ and $R^7$ are the same or different and represent H or $C_{1-6}$ alkyl, with the proviso that if both radicals $R^2$ and $R^3$ represent H, $R^4$ is not $CH_3$ if $R^1$ represents H, OH or Cl, or $R^4$ is not H if $R^1$ represents OH, in the form of their bases or salts of physiologically compatible acids.

Preferred 6-dimethylaminomethyl-1-phenyl-cyclohexane compounds correspond to formula I where $R^1$ represents H, OH or F. Particularly preferred 6dimethylaminomethyl-1-phenyl-cyclohexane compounds are in the form of their diastereoisomers with the configuration of formula Ia, in which the phenyl ring and the dimethylaminomethyl group are situated trans in relation to each other:

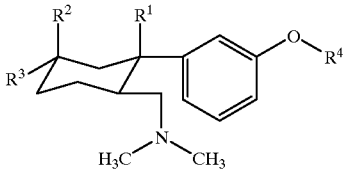

The present invention also relates to a method of peparing 6dimethylaminomethyl-1-phenyl-cyclohexane compounds of formula I, in which $R^1$ represents OH and $R^2$ and $R^3$ are the same or different and represent H, $C_1$–$C_4$ alkyl, benzyl, $CF_3$, Cl or F, with the proviso that at least one of the radicals $R^2$ or $R^3$ is H and $R^4$ represents H, $CH_3$ or an unsubstituted or substituted pyridyl, thienyl, thiazoyl or phenyl group, with the proviso that $R^4$ is neither $CH_3$ nor H if both radicals $R^2$ and $R^3$ represent H, the method being characterised in that a β-dimethylaminoketone of formula II

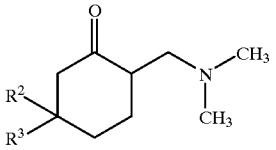

is reacted with an organometallic compound of formula III

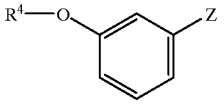

in which Z represents MgCl, MgBr, MgI or Li, to form a compound of formula I.

The reaction of a β-dimethylaminoketone with a Grignard compound of formula III or with an organolithium compound of formula III can be conducted in an aliphatic ether, for example diethyl ether and/or tetrahydrofuran, at a temperature between −70° C. and +60° C. Organolithium compouds of formula III can be obtained by the reaction of a compound of formula III, in which Z represents Cl, Br or I, with an n-butyllithium/hexane solution, for example, by halogen/lithium exchange. On the reaction of a β-dimethylaminoketone of formula II with an organometallic compound, 6-dimethylaminomethyl-1-phenyl-cyclohexane compounds are obtained with the preferred relative configuration of formula Ia.

β-dimethylaminoketones of formula II are obtainable from ketones of formula IV

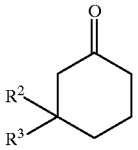

by reaction with dimethylaminohydrochloride and formaldehyde in glacial acetic acid or in a $C_1$–$C_4$ alkyl alcohol, or by reaction with dimethylammonium methylene chloride in acetonitrile catalysed by acetyl chloride (Synthesis 1973, 703; Tietze, Eicher in "Reaktionen und Synthesen im Organisch-Chemischen Praktikum" ["Reactions and Synthesis in the Practice of Organic Chemistry"], Thieme-Verlag, Stuttgart 1991, page 189). The diastereoisomeric β-dimethylaminoketones produced by the aminomethylation reaction can be obtained as pure diastereoisomers, either by separating them by column chromatography or by the fractional crystallisation of their hydrochlorides from an organic solvent, for example 2-butanone and/or acetone.

The present invention further relates to a method of preparing 6-dimethylaminomethyl-1-phenyl-cyclohexane compounds of formula I, in which $R^1$ is OH, one of the radicals $R^2$ or $R^3$ represents H and the other represents OH, O—$C_1$–$C_4$-alkyl or $OCH_2C_6H_5$, and $R^4$ represents H, $CH_3$ or an unsubstituted or substituted pyridyl, thienyl, thiazoyl or phenyl group, which is characterised in that a β-dimethylaminoketone with a spirocyclic acetal structure of formula V

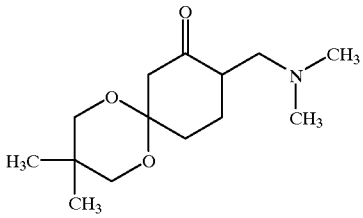

is reacted with an organometallic compound of formula III

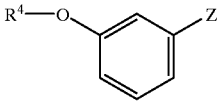

in which Z represents MgCl, MgBr, MgI or Li, to form a compound of formula VI

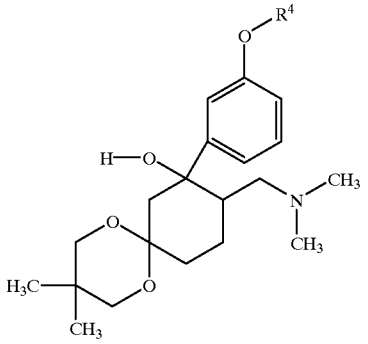

the compound of formula VI which is obtained is converted into the corresponding ketone derivative of formula VIII

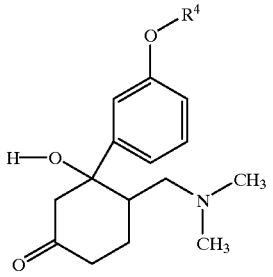

by proton-catalysed deacetylation and the ketone derivative obtained is subsequently reduced with a complex alkali metal hydride to form a compound of formula I in which one of the radicals $R^2$ or $R^3$ represents OH, and if desired the compound of formula I which is obtained by reduction is converted, after conversion into an alkali salt with a $C_1$–$C_4$ alkyl or benzyl halide, into a compound of formula I in which one of the radicals $R^2$ or $R^3$ represents O—$C_1$–$C_4$-alkyl or $OCH_2C_6H_5$.

The reduction of a compound of formula VIII is preferably carried out with sodium borohydride or lithium aluminium hydride in an organic solvent, for example tetrahydrofuran, diethyl ether and/or a $C_2$–$C_4$ alkyl alcohol. If a compound in which $R^2$ or $R^3$ represents $OC_1$–$C_4$-alkyl or $OCH_2Ph$ is to be obtained by the method according to the invention, the compound obtained by reduction is converted with an alkali hydride, for example sodium and/or potassium hydride, in a solvent such as dimethylformamide into the corresponding alkali salt compound and is subsequently reacted with a $C_1$–$C_4$ alkyl or benzyl halide.

β-dimethylaminoketones with a spirocyclic acetal structure of formula V are obtainable from 9-dimethylaminomethyl-3,3-dimethyl-1,5-dioxa-spiro[5,5] undecan-8-one of formula VII

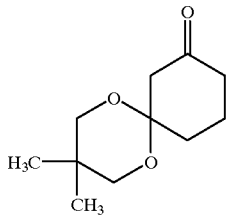

which is accessible by the targeted monoacetylation of cyclohexane-1,3dione, by reaction with dimethylammonium ethylene chloride in acetonitrie catalysed by acetyl chloride (Synthesis 1973, 703; Tietze, Either in "Reaktionen und Synthesen im Organisch-Chemischen Praktikum", Thieme-Verlag, Stuttgart 1991, page 189).

The present invention also relates to a method of preparing 6-dimethylaminomethyl-1-phenyl-cyclohexane compounds of formula I, in which $R^1$ is H, and $R^2$ and $R^3$ are the same or different and represent H, $C_1$–$C_4$ alkyl, benzyl $CF_3$, $OCH_2C_6H_5$ or F, with the proviso that at least one of the radicals $R^2$ or $R^3$ is H, and $R^4$ represents H, $CH_3$ or an unsubstituted or substituted pyridyl, thienyl, thiazoyl or phenyl group, which is characterised in that a compound of formula I in which $R^1$ is Cl is reacted with zinc borohydride, zinc cyanoborohydride or tin cyanoborohydride in an ether, or a compound of formula I in which $R^1$ is OH is reacted with Raney nickel in a $C_2$–$C_4$ alkyl alcohol.

The reaction of a compound of formula I, in which $R^1$ is Cl, with a borohydride, is preferably conducted in diethyl ether and/or tetrahydrofuran at a temperature between 0° and 30° C. The reaction of a compound of formula I, in which $R^1$ is OH, with Raney nickel is preferably conducted in a $C_2$–$C_4$ alkyl alcohol at a temperature between 70° and 100° C. (J. Org. Chem 59, 6895 (1994); and Angew. Chem 95, 568 (1983)).

Cyclohexane compounds of formula I, in which $R^1$ is H, one of the radicals $R^2$ or $R^3$ represents H and the other represents Cl, and $R^4$ represents H, $CH_3$ or an unsubstituted or substituted pyridyl, thienyl, thiazoyl or phenyl group, are obtainable from the corresponding cyclohexane compounds of formula I, in which one of the radicals $R^2$ or $R^3$ is H and the other is OH and $R^1$ and $R^4$ have one of the meanings given above, by reaction with thionyl chloride or hydrolchloride acid/zinc chloride in the known manner (J. Chem. Soc. 1943, 636; J. Org. Chem. 17, 1116 (1952)).

The present invention also relates to a method of preparing 6-dimethylaminomethyl-1-phenyl-cyclohexane compounds of formula I, in which $R^1$ is H, $R^2$ and $R^3$ are the same or different and represent H, $C_1$–$C_4$ alkyl, benzyl, $CF_3$ or F, with the proviso that at least one of the radicals $R^2$ or $R^3$ is H and $R^4$ represents $CH_3$, which is characterised in that a compound of formula I where $R^1$ is Cl is hydrogenated in the presence of a palladium catalyst in a $C_1$–$C_4$ alkyl alcohol. The hydrogenation is preferably conducted at a pressure between 1 and 100 bar and at a temperature between 20° and 80° C.

Compounds of formula I, in which $R^1$ is H, $R^2$ and $R^3$ are the same or different and represent H, a $C_1$–$C_4$ alkyl, benzyl, $CF_3$ or F, and $R^4$ is H, can be obtained from the corresponding methoxyphenyl compounds by heating for several hours with concentrated hydrobromic acid (Chem. Rev. 54, 615 (1954); J. Am. Chem. Soc. 74, 1316 (1952)).

Cyclohexane compounds of formula I, in which $R^1$ is Cl and none of the radicals $R^2$ and $R^3$ represents OH, are obtainable by the reaction of a compound of formula I, in which $R^1$ is OH, in the form of the free base or as the hydrochloride with thionyl chloride in the absence of a solvent at a temperature between 0° and 20° C. In this method, chlorine exchange proceeds with the configuration being maintained. Cyclohexane compounds of formula I where $R^1$ is Cl and $R^2$ or $R^3$ are OH are obtainable in the manner known in the art from the corresponding compounds in which $R^1$ is Cl and $R^2$ or $R^3$ is $OCH_2C_6H_5$.

The present invention also relates to a method of preparing 6-dimethylaminomethyl-1-phenyl-cyclohexane compounds of formula I, in which $R^1$ is F, $R^2$ and $R^3$ are the same or different and represent H, a $C_1$–$C_4$ alkyl, benzyl $CF_3$, $OCH_2C_6H_5$, Cl or F, with the proviso that at least one of the radicals $R^2$ or $R^3$ is H and $R^4$ represents $CH^3$ or an unsubstituted or substituted pyridyl, thienyl, thiazoyl or phenyl group, which is characterised in that a compound of formula I in which $R^1$ is OH is reacted with dimethylaminosulphur trifluoride. The reaction is preferably conducted in an organic solvent, for example dichloromethane, 1,1,2-trichloroethane and/or toluene, at a temperature between −50° and +30° C. (Org. Reac. 35, 513 (1988)).

Compounds of formula I, in which $R^1$ is F, $R^2$ and $R^3$ are the same or different and represent H, a $C_1$–$C_4$ alkyl, benzyl, $CF_3$, $OCH_2C_6H_5$, Cl or F, with the proviso that at least one of the radicals $R^2$ or $R^3$ is H and $R^4$ represents H, can be obtained by the reaction of compounds of formula I, in which $R^1$ represents OH and $R^4$ represents a trialkylsilyl group, with dimethylammonium sulphur trifluoride and subsequent cleavage of the silyl ether with aqueous mineral acids. The dimethyl-tert.-butylsilyl group is a preferred trialkylsilyl group.

A further possible way of obtaining 6dimethylaminomethyl-1-phenyl-cyclohexane compounds of formula I, in which $R^1$ represents OH or H, $R^4$ represents H and neither of the two radicals $R^2$ and $R^3$ represents Cl, F or $CH_3$, consists of the selective ether cleavage, with diisobutylaluminium hydride, of a 6-dimethylaminomethyl-1-(3-methoxyphenyl)-cyclohexane compound, which is preferably conducted in an aromatic hydrocarbon, for example toluene, at a temperature between 60° and 130° C. (Synthesis, 1975, 617).

Furthermore, 6-dimethylaminomethyl-1-phenyl-cyclohexane compounds of formula I, in which $R^1$ represents OH, H or F and $R^4$ represents H, and $R^2$ and $R^3$ are the same or different and represent H, $C_1$–$C_4$ alkyl, benzyl, $CF_3$, F, Cl, OH or O—$C_{1-4}$-alkyl, can be obtained from the corresponding 6-dimethylaminomethyl-1-(3-benzyloxyphenyl)-cyclohexane compounds by reductive debenzylation. Debenzylation is preferably conducted in the presence of platinum or palladium on a support material in the presence of hydrogen in a solvent, for example acetic acid and/or a $C_1$–$C_4$ alkyl alcohol, at a pressure between 1 and 100 bar and at a temperature between 20° and 100° C.

6-dimethylaminomethyl-1-phenyl-cyclohexane compounds of formula I, in which $OR^4$ represents a phosphate, carbonate, carbamate, carboxylate, aryloxy or heteroaryloxy group, can be obtained by the reaction of the corresponding 6-dimethylaminomethyl-1-(3-hydroxyphenyl)-cyclohexane compounds in the form of their alkali salts with an alkali salt of a dialkylchlorophosphate, with an alkyl chloroformate, with an aryl or heteroaryl isocyanate, with a carboxylic acid chloride or with an aryl or heteroaryl halide. The reactions are usually conducted in a solvent, for example toluene, dichloromethane, diethyl ether and/or tetrahydrofuran, at temperatures between −15° C. and +110° C. (Drugs of the Future 16.443 (1991); J. Med. Chem. 30, 2008 (1989) and 32, 2503 (1989); J. Org. Chem. 43, 4797 (1978); Tetrahedron Lett 1977, 1571; J. Pharm. Sci. 57, 774 (1968)). The reactions with an aryl or heteroaryl halide art conducted in the presence of copper powder and/or a copper(I) halide as a catalyst.

6-dimethylaminomethyl-1-phenyl-cyclohexane compounds of formula I, in which $OR^4$ is an amino acid group, can be obtained by the reaction of the corresponding 6-dimethylaminomethyl-1-(3-hydroxyphenyl)-cyclohexane compound with the corresponding 2-t-butoxycarbonylamino-carboxylic acid using triethylamine and coupling reagents, for example benzotriazol-1-yl-oxy-tripyrrolidinophosphonium hexafluorophosphate, in a solvent, for example dichloromethane.

The compounds according to the invention can be converted with physiologically compatible acids, for example hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid and/or aspartic acid, into the salts thereof in the manner known in the art. Salt formation is preferably conducted in a solvent, for example diethyl ether, an acetic acid alkyl ester, acetone and/or 2-butanone. Trimethylchlorosilane in the presence of water in one of the aforementioned solvents is also suitable for the preparation of the hydrochlorides.

The compounds according to the invention have a pronounced analgesic effect and are toxicologically harmless. They are therefore suitable as pharmaceutical active ingredients. Accordingly, the present invention also relates to the use of a 6-dimethylaminomethyl-1-phenyl-cyclohexane compound of formula I as an active ingredient in drugs, preferably as an active ingredient in pain-killing drugs.

In addition to at least one 6-dimethylaminomethyl-1-phenyl-cyclohexane compound, drugs according to the invention contain support materials, fillers, solvents, diluents, colorants and/or binders. The selection of the auxiliary materials and of the amounts to be used depends upon whether the drug is to be applied orally, intravenously, intraperitoneally, intradermally, intramuscularly, intranasally or locally, for example for infections of the skin, of the mucous membranes and of the eyes. Preparations in the form of tablets, dragees, capsules, granules, drops, juices and syrups are suitable for oral application. Solutions, suspensions, readily reconstitutable dry preparations and sprays are suitable for parenteral application. Compounds according to the invention as a deposit in a dissolved form or in a patch, optionally with the addition of agents which promote dermal penetration, are examples of suitable percutaneous forms of application. The compounds according to the invention can be released in a delayed manner from forms of preparations which can be applied orally or percutaneously.

The amount of active ingredient to be administered to the patient varies depending on the weight of the patient, on the type of application, on the indication and on the severity of the illness. 10 to 500 mg of at least one 6-dimethylaminomethyl-1-phenyl-cyclohexane compound of formula I are usually applied per kg.

EXAMPLES

Petroleum ether with a boiling range of 50°–70° C. was used unless indicated otherwise. The term "ether" denotes diethyl ether.

Silica gel 60 (0.040–0.063 mm) supplied by E. Merck, Darmstadt, was used as the stationary phase for column chromatography.

Thin-layer chromatography investigations were performed using ready-for-use HPTLC plates of silica gel 60 F 254, supplied by E. Merck, Darmstadt.

Racemate separations were performed on a Chiracel OD column.

The mixture ratios of the mobile phases for all the chromatographic investigations are always given in volume/volume.

RT denotes room temperature; m.p. denotes melting point.

Example 1

(−)-(1S,2S)-3-(2-dimethylaminomethyl-1-fluoro-cyclohexyl)-phenol hydrochloride (−1)

1st Step (−)-(1S,2S)-1-(3-benzoyloxo-phenyl)-2-dimethylaminomethyl-cyclohexanol hydrochloride (−2)

The base was released from (−)-(1S,2S)-3-(2-dimethylaminomethyl-1-hydroxy-cyclohexyl)-phenyl hydrochloride with aqueous sodium hydrogen carbonate solution/dichloromethane, and the dichloromethane was removed by distillation after drying the solution. 135 g (545 mmole) base were dissolved in 675 ml of dry dimethylformamide and mixed in several portions with 29.1 g of 50% sodium hydride. After adding 69 ml (594 mmole) benzoyl chloride the mixture was heated at 70° C. for three hours. The reaction mixture was then cooled to room temperature and poured on to ice water. It was extracted three times with 150 ml ethyl acetate each time. After drying the organic phases over magnesium sulphate, the solvent was distilled off. The residue (204 g) was taken up in 1000 ml 2-butanone and mixed with 76 ml (600 mmole) trimethylchlorosilane and 10.9 ml water. 190 g of hydrochloride (−2) (93% theoretical) with a melting point of 207°–210° C. crystallised out at room temperature.

$[\alpha]^{RT}_{D}$=−27.0° (c=1.02; methanol)

2nd Step (−)(1S,2S)-[2-(3-benzoyloxy-phenyl)-2-fluoro-cyclohexyl methyl]-dimethylamine (−3)

147.7 g (435 mmole) (−2), dissolved in 1500 ml of dry dichloromethane, were added dropwise at −40° C. to a solution of 80.6 g (500 mmole) diethylamino-sulphur trifluoride in 450 ml of dry dichloromethane. After the addition was complete, the mixture was stirred for 120 minutes at this temperature and subsequently heated to room temperature. After stirrig for a further one hour at room temperature the mixture was cooled to 0°–5° C. and hydrolysed with 500 ml water. The aqueous phase was extracted twice with 200 ml dichloromethane. After drying the organic phases the solvent was removed by distillation. The crude mixture obtained (185 g) was divided into four portions. Each portion was introduced on to an 8×50 cm column packed with silica gel and eluted with 1:1 ethyl acetate/methanol. In total, 103 g (69% theoretical) of base (−3) were obtained as a light yellow, viscous oil.

3rd Step (−)-(1S,2S)-3-(2-dimethylaminomethyl-1-fluoro-cyclohexyl)-phenol hydrochloride (−1)

7.75 g (22.7 mmole) of (−3) were dissolved in 40 ml of dry methanol and introduced into a hydrogenation apparatus with 2.0 g palladium on activated carbon (10% Pd). 430 ml hydrogen were consumed after stiring for 35 minutes at room temperature. The catalyst was removed by filtration, and the methanol was removed by distillation. 6.3 g of base were obtained, from which 4.9 g (75% theoretical) of hydrochloride (−1) were obtained with trimethylchlorosilane/water in 2-butanone/acetone (1/1).

m.p.: 188°–190° C. $[\alpha]^{RT}_{D}$=29.6° (c=1.02; methanol)

Example 2

(+)-(1R,2R)-3-(2-dimethylaminomethyl-1-fluoro-cyclohexyl)-phenol hydrochloride (+1)

Enantiomer (+1) was obtained in a yield of 48% theoretical from (+)-(1R,2R)-3-(2-dimethylaminomethyl-1-hydroxy-cyclohexyl)-phenol hydrochloride, under the conditions given in Example 1.

m.p.: 188°–190° C. $[\alpha]^{RT}_{D}$=+28.3° (c=1.00; methanol)

Example 3

(+)-(1R,2R)-[2-chloro-2-(3-methoxy-phenyl)-cyclohexylomethyl]-dimethylamine hydrochloride (+4)

10 g (33.4 mmole) (+)-(1R,2R)-2-dimethylaminomethyl-1-(3-methoxy-phenyl)-cyclohexanol hydrochloride were mixed with 10 ml thionyl chloride at room temperature. Nitrogen was subsequently passed for two hours over the reaction mixture to remove excess thionyl chloride. After adding a further 10 ml thionyl chloride, the reaction mixture was allowed to stand for 12 hours before excess thionyl chloride was removed again over 2.5 hours with the aid of a stream of nitrogen. After drying, the residue was dissolved in 50 ml of ice-old 2-butanone and mixed with 50 ml diisopropyl ether with stiring, whereupon the hydrochloride crystallised out. For completion, the suspension was stirred for another two hours with ice bath cooling. 5.9 g (55% theoretical) of (+4) were obtained.

m.p.: 120°–121° C. (decomposition) $[\alpha]^{RT}_{D}$=+4.7° (c=0.91; methanol)

Example 4

(−)-(1S,2S)-[2-chloro-2-(3-methoxy-phenyl)-cyclohexylomethy]-dimethylamine hydrochloride (−4)

Enantiomer (−4) was obtained in a yield of 55% theoretical from (−)-(1S,2S)-2-dimethylaminomethyl-1-(3-methoxy-phenyl)-cyclohexanol hydrochloride under the conditions given in Example 3.

m.p.: 120°–122° C. $[\alpha]^{RT}_{D}$=−5.2° (c=0.93; methanol)

Example 5

(+)-(1R,2R)-3-(1-chloro-2-dimethylaminomethyl-cyclohexyl)-phenol hydrochloride (+5)

3.6 g (12.6 mmole) (+)-(1S,2S)-3-(2-dimethylaminomethyl-1-hydroxy-cyclohexyl)-phenol hydrochloride were mixed at room temperature with 3 ml thionyl chloride. The mixture was then stirred for one hour at room temperature. Nitrogen was then passed for two hours over the reaction mixture to remove excess thionyl chloride. After adding a further 4 ml thionyl chloride, the reaction mixture was stirred for two hours at room temperature before excess thionyl chloride was removed over two hours with the aid of a stream of nitrogen. The residue was dissolved in 70 ml 2-butanone and mixed with 50 ml diisopropyl ether with stirring. The hydrochloride which crystallised out was washed three times by decantation with 25 ml 2-butanone. 1.8 g (46% theoretical) of (+5) were obtained after drying.

m.p.: 145°–146° C. (decomposition) $[\alpha]^{RT}_{D}$=+5.2° (c=0.93; methanol)

Example 6

(−)-(1S,2S)-3-(1-chloro-2-dimethylaminomethyl-cyclohexyl)-phenol hydrochloride (−5)

Enantiomer (−5) was obtained in a yield of 48% theoretical from (−)-(1S,2S)-3-(2-dimethylaminomethyl-1-hydroxy-cyclohexyl)phenol hydrochloride under the conditions given in Example 5.

m.p.: 146°–147° C. (decomposition) $[\alpha]^{RT}_{D}$=7.8° (c=1.01; methanol)

Example 7

(+)-(1S,2R)-[2-(3-methoxy-phenyl)-cyclohexylmethyl]-dimethylamine hydrochloride (+6)

46 g of dried zinc chloride were dissolved in 580 ml of dry ether and subsequently added drop-wise to a slurry of 31 g sodium borohydride in 1800 ml ether. After stirring for 12 hours 500 ml were decanted off from the zinc borohydride/sodium chloride suspension obtained and were added drop-wise to 10.2 g (32 mmole) of (+4) in 200 ml of dry ether. The reaction mixture was stirred for 48 hours at room temperature and was then added drop-wise with ice-bath cooling to 40 ml of a saturated ammonium chloride solution. After phase separation, the ether phase was washed twice with saturated common salt solution and the solvent was removed by distillation under vacuum after drying over sodium sulphate. 9.6 g of an amine-borane complex were obtained, which was dissolved in 100ml of dry methanol to isolate the free base. After adding 7.5 g triphenylphosphine, the mixture was heated for 18 hours under reflux. After removing the solvent by distillation, the residue was mixed with 100 ml of 5% hydrochloric acid, and the hydrochloric acid phase was then washed twice with 50 ml ether. Thereafter the hydrochloric acid phase was made alkaline with concentrated sodium hydroxide solution whilst being cooled in an ice bath and was shaken twice with 50 ml dichloromethane. After drying the combined organic phases over sodium sulphate the solvent was distilled off under vacuum and the remaining residue (7.8 g) was taken up in 2-butanone. After adding trimethylchlorosilane/water, 6.9 g (76% theoretical) of hydrochloride (+6) crystallised out.

m.p.: 203°–204° C. (decomposition) $[\alpha]^{RT}_{D}$=+68.0° (c=1.00, methanol)

Example 8

(−)-(1R,2S)-[2-3-methoxy-phenyl)-cyclohexylmethyl]-dimethylamine hydrochloride (−6)

Enantiomer (−6) was obtained in a yield of 75% theoretical from 10.2 g (32 mmole) (−4) under the conditions given in Example 7 m.p.: 201°–203° C. (decomposition) $[\alpha]^{RT}_{D}$=67.1° (c=1.0; methanol)

Example 9

(+)-(1S,2R)-3-(2-dimethylaminomethyl-cyclohexyl)-phenol hydrochloride (+7)

4.3 g (15 mmole) (+6), obtained according to Example 7, were mixed with 100 ml of concentrated hydrobromic acid. The mixture was then heated for two hours under reflux. After cooling to room temperature, the reaction mixture was concentrated under the vacuum from a water pump. The residue was treated with concentrated sodium hydrogen carbonate solution until an alkaline reaction was obtained. After extracting twice with 50 ml dichloromethane each time, the combined organic phases were dried over sodium sulphate. Dichloromethane was then removed by distillation under vacuum and the residue (4 g) was taken up in 2-butanone. After adding trimethylchlorosilane/water, 3.96 g (98% theoretical) of hyrochloride (+7) crystallised out.

m.p.: 177°–178° C. (decomposition) $[\alpha]^{RT}_{D}$=67.5° (c=1.0; water)

Example 10

(−)-(1R,2S)-3-(2-dimethylaminomethyl-cyclohexyl)-phenol hydrochloride (−7)

Enantiomer (−7) was obtained in 95% yield, under the conditions given in Example 9, from (−6), which was prepared according to Example 8.

m.p.: 174°–176° C. (decomposition) $[\alpha]^{RT}_{D}$=−66.1° (c=0.96; methanol)

Example 11

(−)-(1R,2S)-2,2-dimethylpropionic acid-3-(2-dimethylaminomethyl-cyclohexyl)-phenyl ester hydrochloride (−8)

The base was released with dichloromethane/aqueous sodium hydrogen carbonate solution from enantiomer (−7), which was obtained according to Example 10, and the dichloromethane was removed by distillation after drying the solution. 1.7 g (7.3 mmole) of the base obtained were dissolved in 10 ml of dry dimethylformamide and added drop-wise to a suspension of 400 mg sodium hydride (50%) in 5 ml of dry dimethylformamide. The mixture was then stirred for a further 30 minutes at 50° C. After cooling to room temperture. 1.03 ml (8.4 mmole) 2,2dimethylpropionyl chloride were added drop-wise and the reaction mixture was stirred for a further two hours at room temperature before it was poured on to ice/water. The aqueous phase was extracted three times with 50 ml ether. The combined organic phases were dried over sodium sulphate. After removing the solvent by distillation, 2.3 g of crude mixture were obtained and were introduced on to a 4×30 cm column packed with silica gel. Elution with 7/1 diisopropyl ether/methanol gave 1.75 g base. from which 1.75 g (70% theoretical) of hydrohloride (−8) with a melting point of 218°–219° C. was obtained with trimethylchlorosilane/water in 2-butanone/diisopropyl ether.

$[\alpha]^{RT}_{D}$=3.7° (c=1.07; methanol)

Example 12

(−)-(1R,2S)-{2-[3-(p-ispropyl-phenyl-carbamoyl)-oxy-phenyl]-cyclohexyl-methyl}-dimethylamine hydrochloride (−9)

The base was released with dichloromethane/aqueous sodium hydrogen cabonate solution from enantiomer (−7), which was obtained according to Example 10, and the dichloromethane was removed by distillation after drying the solution. 2.1 g (9.0 mmole) of the base obtained were dissolved in 20 ml of dry toluene and mixed with 1.62 g (10 mmole) 4-isopropylphenyl isocyanate. After stirring for 20 hours at room temperature, the toluene was removed by distillation. The residue (2.5 g) was introduced on to a 5.5×15 cm column packed with silica gel and eluted with 1/1 methanol/ethyl acetate. 1.94 g base were obtained, from which 1.8 g (46% theoretical) of hydrochloride (−9) were obtained with trimethylchlorosilane/water in n-propyl acetate.

m.p.: 156° C. $[\alpha]^{RT}_{D}$=16.3° (c=1.09, methanol)

Example 13

(−)-(1R,2S)-2-acetoxy-benzoic acid-3-(2-dimethylaminomethyl-cyclohexyl)-phenyl ester hydrochloride (−10)

The base was released with dichloromethane/aqueous sodium hydrogen carbonate solution from enantiomer (−7), which was obtained according to Example 10, and the dichloromethane was removed by distillation after drying the solution. 0.7 g (3.0 mmole) of the base obtained were dissolved in 7 ml of dry dichloromethane and mixed at room temperature with 0.6 g (3.24 mmole) 2-acetyl-benzoyl chloride dissolved in 3 ml of dry dichloromethane. After stirring for 20 hours at room temperature, the reaction mixture was mixed with 20 ml sodium hydrogen carbonate solution and the aqueous phase was extracted twice with 10 ml dichloromethane. The organic phases were combined and dried over sodium sulphate. After removing the solvent by distillation, 1.1 g of crude mixture was obtained, and was introduced on to a 3×8 cm column packed with silica gel. Elution with ether gave 0.77 g base, from which 0.77 g (54% theoretical) of hydrochloride (−10) were obtained with trimethylchlorosilane/water in ether.

m.p.: 171°–174° C. $[\alpha]^{RT}_{D}$=27.6° (c=1.15; methanol)

Example 14

(−)-(1R,2S)-carbonic acid-[3-(2-dimethylaminomethyl-cyclohexyl)-phenyl]-ester-isobutyl ester hydrochloride (−11)

The base was released with dichloromethane/aqueous sodium hydrogen carbonate solution from enantiomer (−7), which was prepared according to Example 10, and the dichloromethane was removed by distillation after drying the solution 2.34 g (10 mmole) of the base obtained were dissolved in 11 ml of dry dimethylformamide and added drop-wise to a suspension of 0.54 g sodium hydride (50%) in 5 ml of dry dimethylformamide. The mixture was then stirred for 30 minutes at room temperature. Thereafter, 1.44 ml (11 mmole) isobutyl chloroformate were added drop-wise and the reaction mixture was stirred for a further two hours at room temperature before it was mixed with 40 ml water. The aqueous phase was extracted three times with 50 ml ether. The combined organic phases were dried over sodium sulphate. After removing the solvent by distillation, 3.8 g of crude mixture were obtained and were introduced on to a 3×15 cm column packed with silica gel. Elution with ether gave 2.17 g base, from which 1.5 g (41% theoretical) of hydrochloride (−11) was obtained as a colourless syrup.

$[\alpha]^{RT}_{D}$−33.7° (c=1.16; methanol)

Example 15

(−)-(1R,2S)-4morpholin-4-yl-methyl-benzoic acid-3-(2-dimethylaminomethyl-cyclohexyl)-phenyl ester dihydrochloride (−12)

The base was released with dichloromethane/aqueous sodium hydrogen carbonate solution from enantiomer (−7), which was prepared according to Example 10, and the dichloromethane was removed by distillation after drying the solution. 1.9 g (8.1 mmole) of the base obtained were dissolved in 20 ml of dry dichloromethane and mixed at room temperature with 22 g (9.2 mmole) 4-morpholin-4-yl-methyl-benzoyl chloride hydrochloride (prepared according to U.S. Pat No. 4,623,486). After stirring for 20 hours at room temperature, the reaction mixture was mixed with 50 ml sodium hydrogen carbonate solution and the aqueous phase was extracted three times with 10 ml dichloromethane. The organic phases were combined and dried over sodium sulphate. After removing the solvent by distillation, 2.9 g of crude mixture was obtained, and was introduced on to a 4×20 cm column packed with silica gel. Elution with 2/1 diisopropyl ether/methanol gave 0.77 g base, from which 0.41 g (10% theoretical) of dihydrochloride (−12) were obtained with trimethylchlorosilane/water in ether.

m.p.: 234°–236° C. $[\alpha]^{RT}_{D}$=26.8° (c=1.00; methanol)

Example 16

(+)-(2S,3S)-2-amino-3-methyl-pentanoic acid-(1R,2S)-3-(2-dimethylaminomethyl-cyclohexyl)-phenyl ester dihydrochloride (+13)

1st Step (−)-(2S,3 S)-2-tert.-butoxycarbonylamino-3-methyl-pentanoic acid-(1R,2S)-3-(2-dimethylaminomethyl-cyclohexyl)-phenyl ester (−14)

The base was released with dichloromethane/aqueous sodium hydrogen carbonate solution from enantiomer (−7), which was prepared according to Example 10, and the dichloromethane was removed by distillation after drying the solution. 2.1 g (9.8 mmole) of the base obtained were dissolved in 140 ml of dry dichloromethane and mixed in succession at room temperature with 2.19 g (9.5 mmole) (−)-(2S,3S)-2-tert.-butoxycarbonyl-amino-3-methyl-pentanoic acid monohydrate, 2.63 ml (19 mmole) triethylamine and 4.94 g (9.5 mmole) benzotriazol-1-yl-oxy-tripyrrolidino-phosphonium hexafluorophosphate. After stirring for 2 hours at room temperature, the solvent was distilled off and the residue (10.1 g) was introduced on to a 7×40 cm column packed with silica gel. Elution with 1/1 ethyl acetate/methanol gave 2.66 g of base (−14).

2nd Step (+)-(2S,3S)-2-amino-3-methyl-pentanoic acid-(1R,2S)-3-(2-dimethylamiomethyl-cyclohexyl)-phenyl-ester hydrochloride (+13)

2.66 g (5.7 mmole) of (−14) were dissolved in 60 ml of dry dichloloromethane and mixed with 0.23 ml water (13 mmole) and 2.52 ml (19.5 mmole) trimethylchlorosilane. The mixture was then stirred for 20 hours at room temperature. After adding 100 ml ether, 2.1 g (56% theoretical) of hydrochloride (+13) crystallised out.

m.p.: 154° C. (decomposition) $[\alpha]^{RT}_{D}$=+16.6° (c=1.05; methanol)

Example 17

(−)-(1R,25)-dimethyl-{2-[3-(6-methyl-pyridin-2-yloxy)-phenyl]cyclohexyl-methyl}-amnine dihydrochloride (−15)

The base was released with dichloromethane/aqueous sodium hydrogen carbonate solution from enantiomer (−7), which was prepared according to Example 10, and the dichloromethane was removed by distillation after drying the solution. 2.1 g (9.0 mmole) of the base obtained were dissolved in 10 ml of dry dimethylformamide and added drop-wise to a suspension of 475 mg sodium hydride (50%) in 5 ml of dry dimethylformamide. The mixture was then stilred for 10 minutes at 60° C. 1.5 ml (13.7 mmole) 2-chloro-6-methylpyridine were added drop-wise at this temperature. After adding 30 mg copper powder and 30 mg copper(I) chloride, the reaction mixture was stirred for 7 hours at 140° C. before cooling to room temperature. The reaction mixture was mixed with 50 ml water and the aqueous phase was extracted three times with 50 ml ether. The organic phases were combined, washed with 10 ml sodium hydroxide solution and then with 10 ml water and dried over sodium sulphate. After removing the solvent by distillation, 3.2 g of crude mixture were obtained and were introduced on to a 5×20 cm column packed with silica gel. Elution with 99.5/0.5 ether/concentrated ammonia solution gave 1.0 g base, from which 1.89 g (53% theoretical) of dihydrochloride (−15) was obtained with trimethylchlorosilane/water in 2-butanone/ethyl acetate.

m.p.: 60° C. (sintering) $[\alpha]^{RT}_{D}$=44.6° (c=1.0; methanol)

Example 18

(1RS,3SR,6RS)-6-dimethylaminomethyl-1-(3-methoxy-phenyl)-cyclohexane-1,3-diol hydrochloride (16) and (1RS,3RS,6RS)-6-dimethylaminomethyl-1-(3-methoxy-phenyl)-cyclohexane-1,3-diol hydrochloride (17)

1st Step 9-dimethylaminomethyl-3,3-dimethyl-1,5-dioxa-spiro[5,5]undec-8-one hydrochloride (18)

125 g (630 mmole) 3,3-dimethyl-1,5-dioxa-spiro[5,5]undecan-8-one, which was obtained by the azeotropic acetylation of cyclohexane-1,3-dione with 2,2-dimethylpropane-1,3-diol in toluene as a solvent using p-toluenesulphonic acid as a catalyst, and 59 g (630 mmole) dimethylammonium methylene chloride were stirred at room temperature in 400 ml of dry acetonitrile. After adding 1 ml acetyl chloride the mixture was stirred for a further 3 hours at room temperature, whereupon a clear colourless solution was obtained. 800 ml of dry ether were then added drop-wise to the reaction mixture, whereupon the hydrochloride crystallised out. 158 g of (18) were obtained (98% theoretical).

2nd Step (8RS,9RS)-9-dimethylaminomethyl-8-(3-methoxy-phenyl)-3,3-dimethyl-1,5-dioxo-spiro[5,5]undecan-8-ol (19)

20 ml (158 mmole) 1-bromo-3-methoxybenzene, dissolved in 100 ml of dry tetrahydrofuran, were added drop-wise to 3.88 g (160 mmole) magnesium turnings in 10 ml of dry tetrahydrofuran so that the reaction mixture boiled gently. After the addition of 1-bromo-3-methoxybenzene was complete, the mixture was heated for one hour under reflux and was thereafter cooled to 5°–10° C. The base was, released from hydrochloride (18) from step 1 with dichloromethane/sodium hydroxide solution and the dichloromethane was removed by distillation after drying the solution. 32.7 g (150 mmole) of the base obtained were dissolved in 50 ml of dry tetrahydrofuran and added to the Grignard solution. The reaction mixture was allowed to stand overnight and was then cooled to 5°–10° C. again. The Grignard solution was decomposed by the addition of 140 ml of 20% ammonium chloride solution. The reaction mixture was diluted with 200 ml of 1/1 ether/tetrahydrofuran, and the organic phase was separated off and extracted twice with 100 ml ether. The combined organic phases were dried over sodium sulphate. After removing the solvent by distillation, the residue (43.6 g) was introduced on to an 8×50 cm column packed with silica gel and extracted with 1/1 ethyl acetate/methanol. The base obtained was again introduced on to a 5×13 cm column packed with silica gel and eluted with 1/1 diisopropyl ether/methanol. 22.1 g base (42% theoretical) were obtained as a light yellow, viscous oil.

3rd Step (3RS,4RS)-4-dimethylaminomethyl-3-hydroxy-3-(3-methoxy-phenyl)-cyclohexanone (20)

61.8 g (176 mmole) of base (19) from step 2 were dissolved in 800 ml tetrahydrofuran and cooled to 0°–5° C. 800 ml of aqueous hydrochloric acid (conc. hydrochloric acid/water=⅕) were added over 30 minutes at this temperature. The mixture was then stirred for a further one hour at room temperature before it was cooled again to 0°–5° C. 200 ml concentrated sodium hydroxide solution were added at this termperature. The reaction mixture was then extracted three times with 250 ml ether. The combined organic phases were dried over sodium sulphate. After removing the solvent by distillation, the residue (55 g) was introduced on to an 8×50 cm column packed with silica gel and eluted with 7/1 diisopropyl ether/methanol and then with 4/1 ethyl acetate/methanol. The base obtained (24.7 g) was taken up in 1000 ml 2-butanone and mixed with trimethylchlorosilane/water. 16.5 g of hydrochloride (20) (24% theoretical) with a melting point of 161°–163° C. crystallised out.

4th Step (1RS,3SR,6RS)-6-dimethylaminomethyl-1-(3-methoxy-phenyl)-cyclohexane-1,3-diol hydrochloride (16) and (1RS,3RS,6RS)-6-dimethylaminomethyl-1-(3-methoxy-phenyl)-cyclohexane-1,3-diol hydrochloride (17)

The base was released with dichloromethane/sodium hydroxide solution from hydrochloride (20), which was prepared according to step 3, and the dichloromethane was removed by distillation after drying the sdlution. 27 g (97 mmole) of the base obtained were dissolved in 300 ml isopropanol and mixed in portions at room temperature with 1.8 g (47.5 mmole) sodium borohydride. The mixture was stirred for one hour at room temperature before it was cooled to 0°–5° C. 68 ml of diluted hydrochloric acid (conc. hydrochloric acid/water=⅓) were added at this temperature. Immediately after the addition, the reaction mixture was made alkaline with concentrated sodium hydroxide solution. After removing the solvent by distillation, the residue (40 g) was taken up in 200 ml water and extracted three times with 50 ml dichloromethane. The combined organic phases were dried over sodium sulphate and the solvent was removed by distillation. The residue (29.6 g) was introduced on to a 7×45 cm column packed with silica gel and eluted firstly with methanol and then with 99.5/0.5 methanol/concentrated ammonia solution. It was possible to obtain 11.3 g of the base of compound (16) and 13.5 g of the base of compound

(17) in this manner. The bases obtained were taken up in 2-butanone and mixed with trimethylchlorosilane/water, whereupon the hydrochlorides crystallised out.

(16): yield: 9.9 g (32% theoretical) m.p.: 263°–264° C.

(17): yield: 13.7 g (45% theoretical) m.p.: 197°–198° C.

Example 19

Enantiomers of (17)

(+)-(1R,3R,6R)-6dimethylaminomethyl-1-(3-methoxy-phenyl)-cyclohexane-1,3-diol hydrochloride (+17) and (−)-(1S,3S,6S)-6-dimethylaminomethyl-1-(3-methoxy-pnenyl)-cyclohexane-1,3-diol hydrochloride (−17)

The base was released from (17) with dichoromethane/sodium hydroxide solution. The dichloromethane was removed by distillation under vacuum after drying the solution. The racemate was then separated on the chiral HPLC column. The hydrochlorides, which had a melting point of 232°–233° C. were prepared from the enantiomers cbticd by reaction with trimethylchlorosilane/water in 2-butanone.

(+17): yield: 42% theoretical $[\alpha]^{RT}_{D}$=+14.0° (c=1.12; methanol)

(−17): yield: 44% theoretical $[\alpha]^{RT}_{D}$=−13.50° (c=0.99; methanol)

Example 20

(1RS,3RS,6RS)-6-dimethylaminomethyl-1-(3-hydroxy-phenyl)-cyclohexane-1,3-diol hydrochloride (21)

The base was released with dichloromethane/sodium hydroxide solution from compound (17), which was obtained according to Example 18. The dichloromethane was removed by distillation after drying the solution. 8.06 g (28.8 mmole) base were dissolved in 70 ml of dry toluene and slowly added drop-wise to 120 ml (144 mmole) of a 1.2 molar solution af diisobutylaluminium hydride in toluene. After the addition was complete, the mixture was heated for 8 hours under reflux and then cooled to room temperature. The reaction mixture was diluted with 50 ml toluene. 13 ml ethanol and then 13 ml water were added drop-wise whilst cooling in an ice bath. After stirring for one hour whilst cooling in the ice bath, the reaction mixture was freed from aluminium salts by filtration, and the residue was washed three times with 50 ml ethyl acetate each time. Thereafter, the combined organic phases were dried and the solvent was removed by distillation. 7.3 g of the base (84% theoretical), which had a melting point of 226°–228° C. were obtained with aqueous hydrochloric acid solution in acetone.

Example 21

Enantiomers of (21)

(+)-(1R,3R,6R)-6-dimethylaminomethyl-1-(3-hydroxy-phenyl)-cyclohexane-1,3-diol hydrochloride (+21) and (−)-(1S,3S,6S)-6-dimethylaminomethyl-1-(3-hydroxy-phenyl)-cyclohexane-1,3-diol hydrochloride (−21)

The base was released from (21) with dichloromethane/aqueous sodium hydrogen carbonate solution. The dichloromethane was removed by distillation under vacuum after drying the solution. The racemate was then separated on the chiral HPLC column. The hydrochlorides, which had a melting point of 217°–219° C., were prepared from the enantiomers obtained with aqueous hydrochloric acid in acetone.

(+21): yield: 40% theoretical $[\alpha]^{RT}_{D}$=11.3° (c=1.04; methanol)

(−21): yield: 40% theoretical $[\alpha]^{RT}_{D}$=11.1° (c=1.02; methanol)

Example 22

(1RS,2RS,5RS)-5-benzyloxy-2-dimethylaminomethyl-1-(3-methoxy-pheny)-cyclohexanol hydrochloride (22)

The base was released with dichloromethane/sodium hydroxide solution from hydrochloride (17), which was prepared according to Example 18, and the dichloromethane was removed by distillation after drying the solution. 4.0 g (14.3 mmole) of the base obtained were dissolved in 30 ml of dry dimethylformamide and added drowise to a suspension of 690 mg sodium hydride (50%) in 5 ml of dry dimethylformamide. The mixture was then stirred for two hours at room temperature. Alter heating to 50° C., 1.81 ml (14.3 mmole) benzyl chloride were added drop-wise, and the reaction mixture was stirred for a further two hours at 65° C. and for 15 hours at room temperature. The reaction mixture was then poured on to ice water. The aqueous phase was extracted three times with 50 ml ether. The organic phases were combined and dried over sodium sulphate. After removing the solvent by distillation, 4.6 g of crude mixture were obtained and were introduced on to a 4×30 cm column packed with silica gel. Elution with 4/1 ethyl acetate/methanol gave 1.5 g base, from which 1.38 g (24% theoretical) of hydrochloride (22), which had a melting point of 138°–139° C., were obtained with trimethylchlorosilane/water in 2-butanone/diisopropyl ether.

Example 23

(1RS,2RS,5SR)-2-dimethylaminomethyl-1-(3-methoxy-phenyl)5-methyl-cyclohexanol hydrochloride (23)

95 ml (750 mmole) 1-bromo-3-methoxybenzene were dissolved in 425 ml of dry tetrahydrofuran and cooled to −75° C. After adding 469 ml (750 mmole) of 1.6 molar n-butyllithium solution in hexane, the mixture was stirred for one hour at −75° C. 82 g (484 mmole) (2RS,5SR)-dimethylaminomethyl-5-methyl-cyclohexanone, prepared from 3-methyl-cyclohexanone, dimethylamine hydrochloride ride and paraformaldehyde in glacial acetic acid and dissolved in 120 ml of dry terahydrofuran, were then added drop-wise. The reaction mixture was heated to room temperature over 2.5 hours.

For the work-up, 200 ml water were added whilst cooling in an ice bath so that the internal temperature did not exceed 15° C. After phase separation, the aqueous phase was extracted three times with 50 ml ethyl acetate. The combined organic phases were dried over sodium sulphate. After removing the solvent by distillation, the residue (148.3 g) was dissolved in 700 ml acetone and mixed with trimethylchlorosilane/water. 67 g (48% theoretical) of hydrochloride (23), which had a melting point of 173°–175° C., crystallised out at 4°–5° C.

Example 24

Enantiomers of (23)

(+)-(1R,2R,5S)-2-dimethylaminomethyl-1-(3-methoxy-phenyl)-5-methyl-cyclohexanol hydrochloride (+23) and (−)-(1S,2S,5S)-2-dimethylaminomethyl-1-(3-methoxy-phenyl)-5-methyl-cyclohexanol hydrochloride (−23)

Enantiomers (+23) and (−23) were prepared under the conditions given in Example 19.

(+23): yield: 43% theoretical m.p.: 151°–152° C. $[\alpha]^{RT}_{D}$=+36.4° (c=1.01; methanol)

(−23): yield: 44% theoretical m.p.: 151°–153° C. $[\alpha]^{RT}_{D}$=−37.7° (c=1.01; methanol)

Example 25

(+)-(1R,2R,5S)-3-(2-dimethylaminomethyl-1-hydroxy-5-methyl-cyclohexyl)-phenol hydrochloride (+24)

Enantiomer (+24) was prepared under the conditions given in Example 20 from the methoxy compound (+23) obtained according to Example 24.

yield: 87% theoretical m.p.: 221°–223° C. $[\alpha]^{RT}_{D}$=+31.0° (c=1.09; methanol)

Example 26

(−)-(1S,2S,5R)-3-(2-dimethylaminomethyl-1-hydroxy-5-methyl-cyclohexyl)-phenol hydrochloride (−24)

Enantiomer (−24) was prepared under the conditions given in Example 20 from the methoxy compound (−23) obtained according to Example 24.

yield: 87% theoretical m.p.: 220°–222° C. $[\alpha]^{RT}_{D}$=+30.1° (c=1.00; methanol)

Example 27

(1RS,2RS,5SR)-3-(2-dimethylaminomethyl-1-hydroxy-5-trifuoromethyl-cyclohexyl)-phenol hydrochloride (25)

1st Step (1RS,2RS,5SR)-1-(3-benzyloxy-phenyl)-2-dimethylaminomethyl-5-trifuoromethyl-cyclohexanol (26)

43.9 g (167 mmole) 3-benzyloxy-1-bromobenzene, dissolved in 200 ml of dry tetrahydrofuran, were added dropwise to 4.06 g (167 mmole) magnesium turnings in 40 ml of dry tetrahydrofuran so that the reaction mixture boiled gently. After the addition of 3-benzyloxy-1-bromobenzene was complete, the mixture was heated for one hour under reflux and was thereafter cooled to 5°–10° C. 30.8 g (139 mmole) (2RS,5SR)-2-dimethylaminomethyl-5-trifluoromethyl-cyclohexanone, prepared from 3-trifluoromethyl-cyclohexanone and dimethylaminomethylene chloride in acetonitrile, dissolved in 80 ml of dry tetrahydrofuran were added at this temperature. The reaction mixture was allowed to stand overnight and was then cooled to 5°–10° C. again. The Grignard solution was decomposed by the addition of 150 ml of 20% ammonium chloride solution. The reaction mixture was diluted with 200 ml of ether, the organic phase was separated off and the aqueous phase was extracted twice with 100 ml ether. The combined organic phases were dried over sodium sulphate. After removing the solvent by distillation, the residue (60.6 g) was introduced on to an 8×50 cm column packed with silica gel and extracted with ethyl acetate/methanol. 27.8 g (50% theoretical) of base (26) were obtained.

2nd Step (1RS,2RS,5SR)-3-(2-dimethylaminomethyl-1-hydroxy-5-trifuoromethyl-cyclohexyl)-phenol hydrochloride (25)

(25) was obtained, under the conditions given in Example 1 (step 3), from (26) from step 1, in a yield of 64% and with a melting point of 228°–230° C.

Example 28

(1RS,2RS ,5RS)-3-(2-dimethylaminomethyl-1-hydroxy-5-trifuoromethyl-cyclohexyl)-phenol hydrochloride (27)

The 5-epimer (27) of compound (25) was prepared, under the conditions given in Example 27, from (2RS,5RS)-2-dimethylaminomethyl-5-trifluoromethyl-cyclohexanone, prepared from 3-trifluoromethyl-cyclohexanone and dimethylaminomethylene chloride in acetonitrile. (27) was obtained in a yield of 27% theoretical and had a melting point of 221°–223° C.

Example 29

(1RS,2RS,5SR)-3-(2-dimethylaminomethyl-1-fluoro-5-trifluoromethyl-cyclohexyl)-phenol hydrochloride (28)

Hydrochloride (28) was obtained in a yield of 24% theoretical and with a melting point of 204°–205° C., under the conditions given in Example 1, steps 2 and 3, from the base (26) obtained according to Example 27 (step 1).

Example 30

(1RS,2RS,5RS)-3-(2-dimethylaminomethyl-1-fluoro-5-trifluoromethyl-cyclohexyl)-phenol hydrochloride (29)

Hydrochloride (29) was obtained in a yield of 22% theoretical and with a melting point of 204° C. under the conditions given in Example 29, from the base (1RS,2RS,5RS)-1-(3-benzyloxy-phenyl)-2-dimethylaminomethyl-5-trifluoromethyl-cyclohexanol obtained according to Example 27 (step 1).

Pharmacological investigations

Testing for analgesia using the tail flick test on mice

The analgesic effectiveness of the compounds according to the invention was investigated in the thermal radiation (tail flick) test on mice using the method of D'Amour and Smith (J. Pharm. Exp. Ther. 72, 74–79 (1941). NMRI mice with a weight between 20 and 24 g were used for this purpose. The animals were placed in a special test cage and the bases of their tails were exposed to the focused thermal radiation from an electric lamp (Rhema Analgesiemeter Type 3010). The lamp intensity was adjusted so that the time from switching on the lamp until the sudden twitching away of the tail (latency of pain) was 3–5 seconds for untreated animals. Before the administration of a compound according to the invention, the animals were pre-tested twice within five minutes and the average value of these measurements was calculated as the pre-test average. The pain measurement was made 20, 40 and 60 minutes after intravenous administration. When the latency of pain increased, the maximum time of exposure was restricted to 12 seconds and an increase in the latent period to >150% of the pre-test average value was assessed as an analgesic effect. In order to determine the dosage-dependency, the respective compound according to the invention was applied in doses increasing logarithmically by a factor of 3–5, which included the threshold and the maximum effective dose each time. The $ED_{50}$ values were determined from the number of analgesic animals by the method of Litchfield and Wilcoxon (J. Pharm. Exp. Ther. 96, 99–113, (1949)). Calculation of the $ED_{50}$ was made at the effective maximum 20 minutes after intraveneous adminstration of the substance.

All the compounds according to the invention which were used exhibited a pronounced analgesic effect. The results are summarised in the following Table.

TABLE

Testing of analgesic using the tail flick test on mice

| Example | Compound according to the invention | $ED_{50}$ (mg/kg intravenously) |
|---|---|---|
| 1 | (−1) | 2.28 |
| 2 | (+1) | 0.64 |
| 5 | (+5) | 2.78 |
| 7 | (+6) | 10.70 |
| 9 | (+7) | 1.13 |
| 10 | (−7) | 5.90 |
| 11 | (−8) | 4.61 |
| 13 | (−10) | 8.71 |
| 14 | (−11) | 5.01 |
| 18 | (17) | 5.54 |
| 19 | (+17) | 3.93 |
| 21 | (+21) | 7.34 |
| Tramadol | — | 13.60 |

We claim:

1. A 6-dimethylaminomethyl-1-phenyl-cyclohexane compound corresponding to formula I:

I

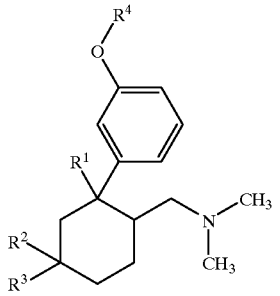

wherein $R^1$ represents H, OH, Cl or F;

$R^2$ represents benzyl, $CF_3$, OH, $OCH_2$-$C_6H_5$, O—$C_{1-4}$-alkyl, Cl or F, $R^3$ represents H, $R^4$ represents H, $CH_3$, $PO(OC_{1-4}\text{-alkyl})_2$, $CO(OC_{1-5}\text{-alkyl})$, CO—NH—$C_6H_4$-$C_{1-3}$-alkyl CO—$C_6H_4$-$R^5$, CO—$C_{1-5}$-alkyl CO—$CHR^6$-$NHR^7$ or an unsubstituted or substituted pyridyl thienyl, thiazoyl or phenyl group;

$R^5$ represents $OC(O)C_{1-3}$-alkyl in the ortho position or $CH_2$-$N(R^8)_2$ in the meta or para position, wherein $R^8$ represents $C_{1-4}$ alkyl or both groups $R^8$ together with N constitute a 4-morpholino radical, and $R^6$ and $R^7$ are each independently selected from H and $C_{1-6}$ alkyl, or a pharmaceutically acceptable acid addition salt thereof.

2. A 6-dimethylaminomethyl-1-phenyl-cyclohexane compound according to claim 1, wherein $R^1$ is H, OH or F.

3. A 6-dimethylaminomethyl-1-phenyl-cyclohexane compound according to claim 1, wherein the compound has the configuration of formula Ia:

Ia

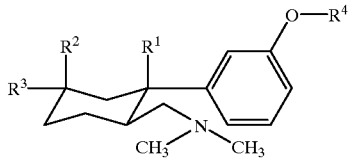

4. A pharmaceutical composition comprising a 6-dimethylaminomethyl-1-phenyl-cyclohexane compound according to claim 1, and at least one pharmaceutical carrier or diluent.

5. A method of relieving pain in a mammal comprising administering to said mammal an effective pain relieving amount of a 6-dimethylaminomethyl-1-phenyl-cyclohexane compound according to claim 1.

*6. A 6-dimethylaminomethyl-1-phenyl-cyclohexane compound corresponding to formula I:*

*I*

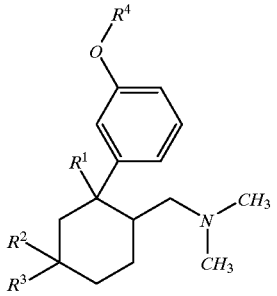

*wherein*

*$R^1$ represents H, OH, Cl or F;*

*$R^2$ represents benzyl, $CF_3$, OH, $OCH_2$-$C_6H_5$, O—$C_{1-4}$-alkyl, Cl or F, or if $R^1$ and $R^4$ are H, $R^2$ may also be H,*

*$R^3$ represents H,*

*$R^4$ represents H, $CH_3$, $PO(OC_{1-4}\text{-alkyl})_2$, $CO(OC_{1-5}\text{-alkyl})$, CO—NH—$C_6H_4$-$C_{1-3}$-alkyl, CO—$C_6H_4$-$R^5$, CO—$C_{1-5}$-alkyl, CO—$CHR^6$-$NHR^7$ or an unsubstituted or substituted pyridyl, thienyl, thiazoyl or phenyl group;*

*$R^5$ represents $OC(O)C_{1-3}$-alkyl in the ortho position or $CH_2$-$N(R^8)_2$ in the meta or para position, wherein $R^8$ represents $C_{1-4}$ alkyl or both groups $R^8$ together with N constitute a 4-morpholino radical, and*

*$R^6$ and $R^7$ are each independently selected from H and $C_{1-6}$ alkyl,*

*or a pharmaceutically acceptable acid addition salt thereof.*

*7. (−)-(1R,2S)-3-(2-dimethylaminomethyl-cyclohexyl)-phenol or a pharmaceutically acceptable acid addition salt thereof.*

* * * * *